United States Patent [19]

Wiley

[11] 4,252,944

[45] Feb. 24, 1981

[54] 4-AMINO-6-(2-CARBOXYPHENYL)-3-MERCAPTO-1,2,4-TRIAZIN-5(4H)-ONE

[76] Inventor: Richard H. Wiley, 8 Roosevelt Cir., Palo Alto, Calif. 94306

[21] Appl. No.: 133,440

[22] Filed: Mar. 24, 1980

[51] Int. Cl.³ .......................................... C07D 253/06
[52] U.S. Cl. .................................................. 544/182
[58] Field of Search ........................................ 544/182

[56] References Cited

U.S. PATENT DOCUMENTS

| | | | |
|---|---|---|---|
| 3,966,715 | 6/1976 | Westphal et al. | 71/93 |
| 4,036,632 | 7/1977 | Westphal et al. | 71/93 |
| 4,058,526 | 11/1977 | Merz et al. | 544/182 |
| 4,113,767 | 9/1978 | Merz | 544/182 |
| 4,151,355 | 4/1979 | Merz | 544/182 |

FOREIGN PATENT DOCUMENTS

| | | |
|---|---|---|
| 2165554 | 7/1973 | Fed. Rep. of Germany . |
| 2460889 | 6/1976 | Fed. Rep. of Germany . |
| 713540 | 8/1954 | United Kingdom . |
| 1182802 | 3/1970 | United Kingdom . |

*Primary Examiner*—John M. Ford

[57] ABSTRACT

4-Amino-6-(2-carboxyphenyl)-3-mercapto-1,2,4-triazin-5(4H)-one is prepared by the reaction of phthalonic acid or its potassium salt with thiocarbohydrazide. The product melts at 180° at which temperature it decarboxylates, resolidifies, and remelts at 235°–240° as the known 6-phenyl derivative. The compound is useful as a selective herbicide.

1 Claim, No Drawings

4-AMINO-6-(2-CARBOXYPHENYL)-3-MERCAPTO-1,2,4-TRIAZIN-5(4H)-ONE

Background of the invention: 6-Substituted-4-amino-3-mercapto-1,2,4-triazin-5(4H)-ones and their derivatives are well-known selective herbicides. Their preparation and use are described in U.S. Pat. No. 3,966,715 and Chem. Ber. 97, 2173 (1964) and Naturwissenschaften 55, 446 (1968). The very real economic and processing problems encountered in the production of a widely used member of the class (a 6-tert.butyl derivative) is detailed in U.S. Pat. No. 4,113,767.

Summary of the invention: The present invention provides a previously unknown member of a class of triazinone herbicides—4-amino-6-(2-carboxyphenyl)-3-mercapto-1,2,4-triazin-5(4H)-one-, and a process for its preparation, which combines useful selective herbicidal properties with an enhanced economic availability. This compound is obtained by oxidation of naphthalene to phthalonic acid, which need not be isolated, and reaction of the latter with thiocarbohydrazide.

It is unpredictable and surprizing that the carboxy group of phthalonic acid (a very strong acid) does not react with thiocarbohydrazide to give the thiazole: 4-amino-5-(2-oxalylphenyl)-3-mercapto-1,2,4-triazole—by the known reaction of carboxylic acids with thiocarbohydrazide (Beyer et al. Annalen 637, 135(1960).

The presence of the carboxy phenyl group in the triazinone contributes an increased but limited water solubility to the triazinone and thus enhances its utility over that of other triazinones which do not have a carboxy group in the molecule and are thus less water soluble. In aqueous solutions at intermediate pH values, the title compound exists as a zwitterion.

The process for the preparation of the title compound and its characteristics are given in the following examples.

Example 1: Potassium phthalonate is prepared as described by Tcherniac, J. Chem. Soc. Vol. 109, p. 1236; Beilstein, Vol. X, p.857 and recrystallized from ethanol. Anal. for $C_9H_5O_3K.0.8H_2O$: Calcd. C, 43.83; H, 2.67; K, 15.83. Found: C, 43.95; H, 2.66; K, 16.00. This salt, 500 mg., and 225 mg. of thiocarbohydrazide are dissolved in 15 ml. of water and heated ten minutes on a steam bath. The pH is adjusted from 4–5 to 1 and the precipitate which forms on standing is collected and dried to give 500 mg. of the title compound. Recrystallized from ethanol-water; mp. 180° (dec., gas evolution, resolidification) 235°–240° (sample inserted in bath at 180° or over or the melting at 180° will not be observed). Anal. Calcd. for $C_{10}H_8N_4O_3S.H_2O$: C, 42.85; H, 3,57; N, 19.86. Found: C, 42,79; H, 3.52; N, 19.31.

Example 2: The potassium phthalonate prepared as in example 1 is converted to the free acid by adsorption of the potassium ion on Dowex-50 ion exchange resin and evaporation of the eluted aqueous solution of the acid. The vacuum dried acid melts at 135°–140° (reported 143°). Anal. Calcd. for $C_9H_6O_5$ $0.17H_2O$: C, 54.85; H, 3.21. Found: C, 54.82; H, 3.15; K, 0.0. This acid, 900 mg., and 500 mg. of thiocarbohydrazide are dissolved in 45 ml. of aqueous ethanol (pH 3) and heated five minutes on the steam bath. The crystals which separate on cooling are collected and vacuum dried to give 1.0 g. of the title compound. Recrystallized from ethanol water, mp. 180° (dec., gas evolution, resolidification) mp. 235°–240°. The sample is inserted in the bath at 180°, otherwise the melting at 180° will not be observed. After the gas evolution ($CO_2$) is complete the sample resolidifies and then melts at 235°–240° with slow heating. The recorded melting point of 4-amino-3-mercapto-6-phenyl-1,2,4-triazin-5(4H)-one, the decarboxylated product, is reported to melt at 231°; 242° (U.S. Pat. No. 3,966,715). Thiocarbohydrazide melts at 180° with decomposition but does not resolidify and remelt at 235°.

Example 3: An aliquot portion (4.7 ml. containing approximately 500 mg. of phthalonic acid based on the amount of reactants used in the preparation and assuming complete conversion to phthalonic acid) of the hydrochloric acid acidified reaction mixture obtained on oxidizing naphthalene according to the above cited procedure is heated with 300 mg. of thiocarbohydrazied in 15 ml. of warm water. The pH is 2. On standing the crystalline product separates and is collected. The yield of dried product, mp. 170–189/230° is 200 mg. Recrystallized from ethanol water, mp. 180/235°.

What is claimed is:
1. 4-Amino-6-(2carboxyphenyl)-3-mercapto-1,2,4-triazin-5(4H)-one.

* * * * *